United States Patent
Meier et al.

[11] Patent Number: 6,102,869
[45] Date of Patent: Aug. 15, 2000

[54] PROCESS AND DEVICE FOR DETERMINING THE CARDIAC OUTPUT

[75] Inventors: Bernd Horst Meier, Darmstadt; Helmut Otto Heinemann, Kelkheim; Harald Foerster, Frankfurt am Main, all of Germany

[73] Assignee: Heinemann & Gregori GmbH, Kelkheim, Germany

[21] Appl. No.: 09/041,463

[22] Filed: Mar. 12, 1998

Related U.S. Application Data

[63] Continuation of application No. PCT/EP96/03918, Sep. 6, 1996, abandoned.

[30] Foreign Application Priority Data

Sep. 12, 1995 [DE] Germany .............. 195 33 663

[51] Int. Cl.⁷ .............. A61B 5/04; A61B 5/02; A61B 5/05
[52] U.S. Cl. .............. 600/506; 600/526; 600/547
[58] Field of Search .............. 600/506, 547, 600/507, 526, 508, 513, 509; 607/28

[56] References Cited

U.S. PATENT DOCUMENTS

| | | | |
|---|---|---|---|
| Re. 30,101 | 9/1979 | Kubicek et al. | 600/526 |
| 4,836,214 | 6/1989 | Sramek | 600/506 |
| 4,852,580 | 8/1989 | Wood | 600/506 |
| 4,898,176 | 2/1990 | Petre | 600/374 |
| 4,951,682 | 8/1990 | Petre | 600/526 |
| 4,953,556 | 9/1990 | Evans | 600/484 |
| 5,000,190 | 3/1991 | Petre | 600/526 |
| 5,203,337 | 4/1993 | Feldman | 600/463 |
| 5,791,349 | 8/1998 | Shmulewitz | 600/547 |

FOREIGN PATENT DOCUMENTS

| | | |
|---|---|---|
| 26 20 285 | 9/1977 | Germany . |
| WO 89/12421 | 12/1989 | WIPO . |
| WO 92/19157 | 11/1992 | WIPO . |

*Primary Examiner*—Max Hindenburg
*Assistant Examiner*—Navin Natnithithadha
*Attorney, Agent, or Firm*—Griffin, Butler, Whisenhunt & Szipl, LLP

[57] ABSTRACT

Procedure and device for determining cardiac output volume which involves applying an electrical potential to create a current flow through tissue of the patient's heart, placing a first measuring electrode on skin of the patient near the heart and inserting a second measuring electrode into the patient's body at a position on an opposite side of the heart from the first measuring electrode so that a straight-line heart-traversing projection extends through the heart between the first and the second measuring electrodes. In one embodiment the second measuring electrode is in a blood vessel and in another embodiment there are a plurality of second measuring electrodes with the best one being determined by Electrocardiogram equipment.

15 Claims, 2 Drawing Sheets

PROCESS AND DEVICE FOR DETERMINING THE CARDIAC OUTPUT

This is a continuation of PCT Application No. PCT/EP96/03918, filed Sep. 6, 1996, now abandoned.

BACKGROUND OF THE INVENTION

The invention relates to a procedure for the measurement of cardiac output in recording the systolic change of impedance of a tissue by placing at least one initial measuring electrode, within the region of an AC/DC electrical signal, in the skin tissue, and a device for the implementation of the procedure.

The quantity of cardiac output is a measuring indicator for pump performance of the heart. It is an authoritative factor for evaluating whether a human organism (or animal) can assumingly resist suggested physical strain (athletes, pilots, astronauts, racing horses). Apart from other parameters, cardiac output is important during operations, to assess a patient's situation.

The previous impedance procedure for the measurement of cardiac output, especially the procedure according to KUBICEK, is based on the AC/DC change of a tissue area including considerable parts of the thorax, which is caused by heart action. The volume change in capacity vessels caused by the systoles, create a measurable change of tissue impedance (under consideration of the hematocrit, the electrode distances and the volume of thoracic cavity), with which cardiac output can be calculated.

An electrical alternating current of a defined frequency and an amperage Im, flows between two current driving electrodes, which define an AC/DC current path in the tissue. Two measuring electrodes are placed between the two driving electrodes and the voltage $U_m=I_m Z$ is measured. In the equation Z is the impedance between the measuring electrodes, whereas cardiac output is derived from changes of dz/dt, depending on time. For this purpose two circular glued electrodes are placed on the neck and on the caudate thorax and a weak alternating current is applied.

BRIEF SUMMARY OF THE INVENTION

In contrast to this, the invention should offer a more precise procedure for the measurement of cardiac output.

The initially mentioned procedure according to the invention includes a second measuring electrode, which is introduced into a vessel essentially opposite the heart, in relation to the first electrode, and is positioned on a specified heart-traversing straight-line projection from the first measuring electrode.

The term "vessel" should be understood in a further sense as any hollow organ, which might be a blood vessel, the esophagus or the trachea. As the invention is used on humans, all hollow organs of the thoracic cavity might be interpreted as a vessel. Compared to the previous procedures of cardiac output measurement, the great advantage of the invention is based on the fact that, impedance changes are measured directly on the heart as the actual object of investigation. Hence, falsifications of the measurements caused by other tissue parts can be excluded. The direct application of an alternating current with an amperage of a few hundred microampere and a frequency of 10 to 400 kHz to the heart does not cause any risk for the organ. The introduction of a second measuring electrode is not problematic. As a functional feature of the invention the placement of the second measuring electrode in the vessel could be controlled by a depiction procedure (i.e. X-ray or sonographic check).

It is recommended to determine the position of the second measuring electrode and its relation to the first measuring electrode via the display of an electro-cardiographic vector signal. For this purpose an electro-cardiographic vector signal should be recorded by the first and the second measuring electrodes. Thus, the intended position of the second measuring electrode is controlled by the specific course of the ECG curve. A placement of the first measuring electrode close to the apex of the heart is recommended for this purpose. Additionally, it is advantageous if a few second electrodes are arranged in axial distance, i.e. on an esophagus catheter in pairs of measuring electrodes, including a first measuring electrode and a second measuring electrode each, registered on an electrocardiogram and the electrode pair whose projection is closest to the heart is determined, and the impedance variables of this pair of electrodes are registered.

It is usual to record the pressure changes of heart chambers. If the volume curve of a heart chamber is additionally recorded by the invented procedure, both signals might be scanned up to a pressure-volume diagram of an interior heart chamber, lying between the two measuring electrodes. From that, output features of the heart chamber might be concluded.

For the purpose of the installation of an alternating current path, a first current driving electrode is advantageously placed on the skin advantageously close to the heart and a second driving electrode is inserted into the vessel, whereby the first and second current driving electrodes are arranged in such a manner, that the specified straight-line projection between the measuring electrodes conforms as much as possible with the defined alternating current path through both current driving electrodes.

Further designs of the procedure are also described herein.

A device carrying out the invented procedure includes a flexible vessel catheter, which is characterized by a sufficient length and a sufficient smallness of diameter. On an electrically isolated outer cover at least one second measuring electrode as well as at least one second axially spaced current driving electrode should be mounted, whereby the measuring electrodes are electrically connected to a measuring conductor inside the catheter, and the current driving electrodes are electrically connected to a current conductor passed through the inside of the catheter, whereby current driving electrodes are connected to an alternating current generator and the measuring electrodes are connected to electronic evaluation equipment.

Practically, the tube catheter contains an axial suction channel, which is open to the second measuring electrode as well as to the second current driving electrode providing orifices to the outside of the catheter, whereby after the connection of the suction channel to a suction pump, a close electrical contact of the second measuring and current electrodes and the tissue outside the catheter is made.

It is recommended to create an additional axial working channel besides the axial suction channel, which is used to insert, for example, an endoscope or other devices (magnetic probes, ultra-sonographic or doppler probes, phonocardiographic probes), improving electrode placement and precision of measurements.

Advantageously, several axially spaced second measuring electrodes can be provided, which are electrically isolated from each other, whose alternate distance could be similar, and which are fixed to the circumference of the catheter.

Additionally, the second current driving electrode should be set above the second measuring electrode, as seen from the end of the catheter.

It is recommended, that the evaluation device, which is connected to the first and the second measuring electrodes has an electrical frequency switch control device, which transfers the low frequency part of the signal to an electrocardiographic apparatus and the high frequency part to an impedance evaluation device.

Further advantageous arrangements of the invention are also disclosed herein.

BRIEF DESCRIPTION OF THE DRAWINGS

The invention is explained in the following text with reference to the drawings.

DETAILED DESCRIPTION OF THE INVENTION

Figure 1:
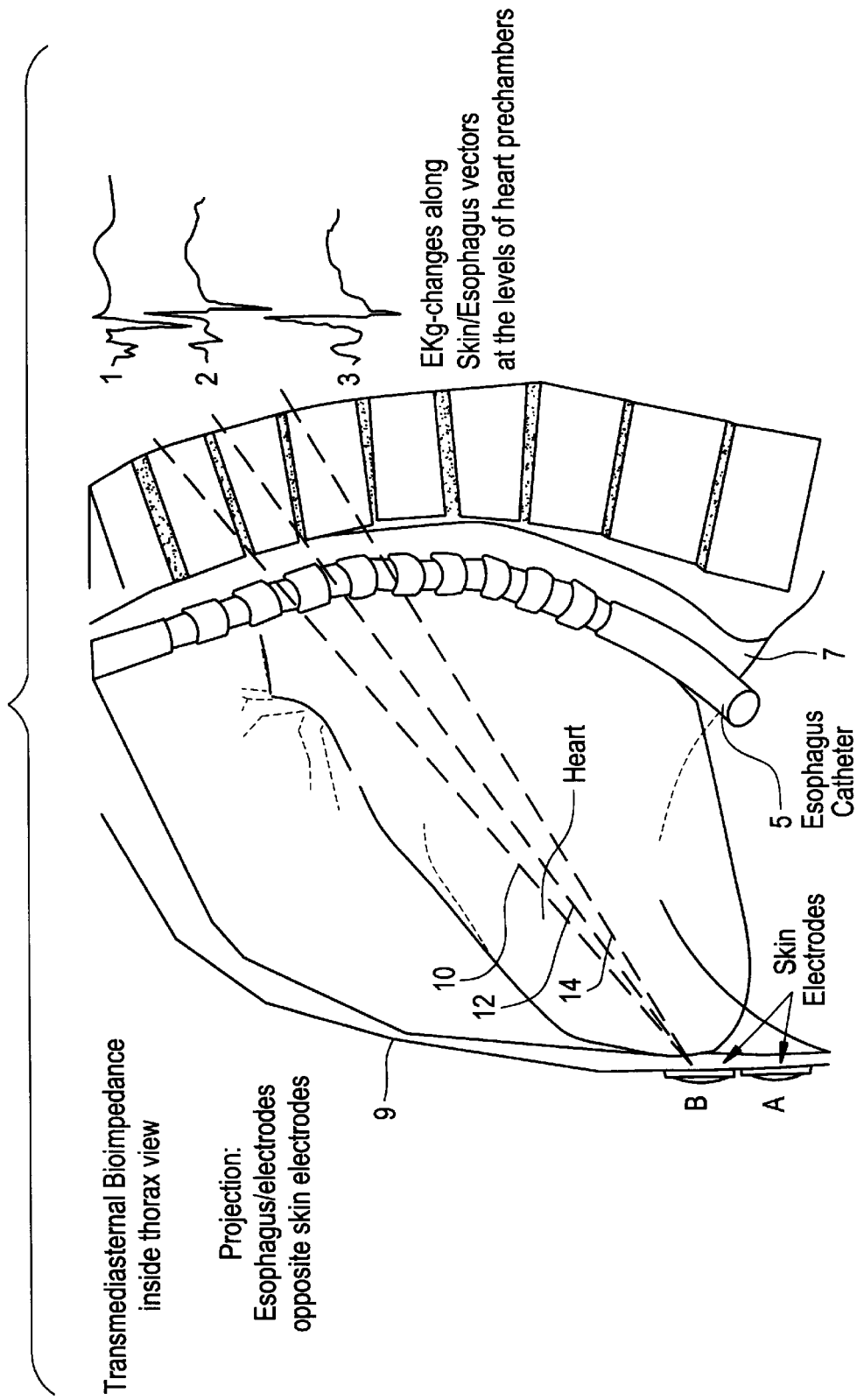
FIG. 1 is a schematic representation of a transmediastinal bioimpedance measurement being taken in a general side view.

According to FIG. 1, a first current driving electrode A, and above this electrode a first measuring electrode B have been fixed to the skin 9 of a volunteer. An esophageal catheter, described throughout as 5, has been inserted into the schematic depiction of an esophagus 7, carrying a plurality of axially spaced measuring electrodes C,D,E,F,G, H,I,J,K,L. Each of the two upper electrodes C/D could be the second current driving electrode, whereas the following electrodes below E, . . . , L could be a second measuring electrode.

The straight-line projections (lines 10, 12, 14) show the measurement lines of the impedance changes between the first measuring electrode B and the second measuring electrode E or F or G.

Curve 1 in the right upper corner of FIG. 1 shows the electrocardiogram, recorded by the measuring electrodes B and E, along Projection 10.

Curve 2 shows the electrocardiogram recorded by measuring electrodes B–F along the projection 12.

Curve 3 is for measuring path B-G along projection 14.

Figure 2:
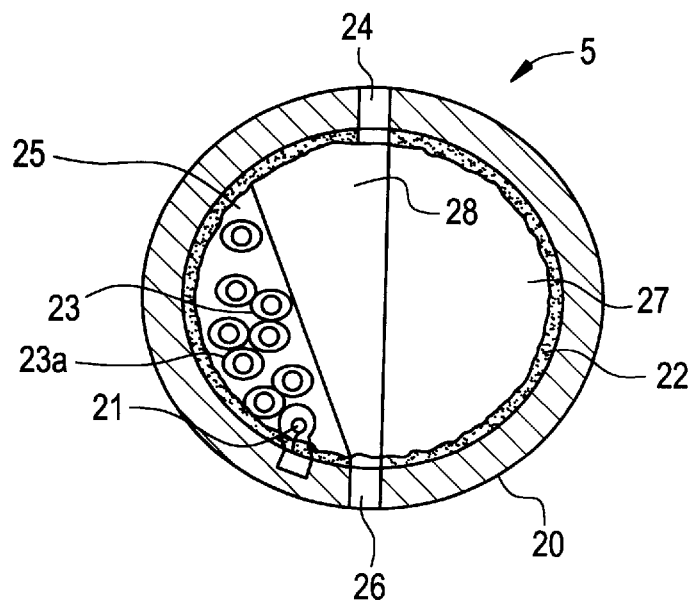
FIG. 2 is an enlarged cross section of an esophageal catheter at an electrode.
Figure 3:
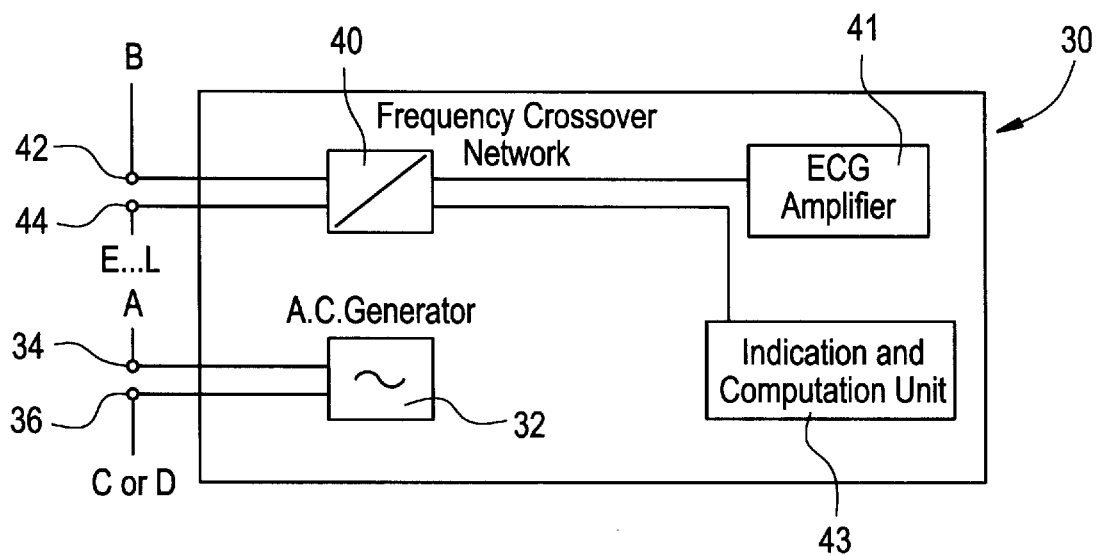
FIG. 3 is a schematic block diagram of an evaluation device for use in this invention.

According to FIG. 2, each of the current driving and measuring electrodes has an external annular electrode 20, which has a high electrical conductivity and is coated with an insulating material 22 on its inside.

The annular electrode 20 and the insulation is provided with diametrical orifices 24, 26 which are used to connect an axial suction channel 28 to the outside of the catheter 5.

A core assembly 23 is led through the insulation to the annular electrode 20 by a soldered joint 21. Each of the other measuring and current driving conductors 23a are connected to their annular measuring or current electrodes in the same way. They are positioned in an axial aligned chamber 25 inside the catheter, which is separated from the suction channel 28.

On the inside of catheter 5 is an axial aligned working channel 27, which is separated from the suction channel, which is used to insert an endoscope or another auxiliary device.

An evaluation device 30 contains an AC generator 32, of which the first output contact 34 is connected to the first current driving electrode A, and the second output contact 36 is connected to one of the second current electrodes C or D. The AC generator 32 generates a current with a frequency of 40 kHz.

The evaluation device 30 further contains one first input measuring terminal 42, connected to the first measuring electrode B, as well as a second measuring terminal 44, which is connected to one of the second input measuring electrodes E, . . . , L.

The two input measuring terminals 42 and 44 are the inputs of the frequence crossover network 40, which transmits the signal parts of approximately 1 Hz from the input measuring terminals 42 and 44 to an ECG-Amplifier 41, and the signal parts of approximately 40 kHz to an indication and computation unit 43. The indication and computation unit 43 calculates and indicates the heart minute volume.

If the input measuring terminal 42 is connected to the measuring electrode B, a number of input measuring terminals 44 could be connected together to an equal number of the second measuring electrodes E, . . . , L, whereby the frequency crossover network 40 can be switched onto the actual measuring terminals 44.

The heart minute volume is determined by the heart frequency and the stroke volume by HZV=f*SV The stroke volume is determined by the following equation:

$$SV = rho * \frac{dZ}{dt} * T * \frac{L*L}{Zo},$$

whereby:

rho is the specific resistance of the blood, which is normally 135 Ohm/cm, and depending on the hematocrite, dZ/dt is the first derivative of the impedance in Ohms/second, T is the injection time in seconds, Zo is the measured mean impedance between the first and the respective second measuring electrode in Ohms.

The last discussed formula is valid for beagles. To calculate stroke volumes for humans, the formula must be multiplied by a factor.

Experiences in Impedance Measurements of Cardiac Output in Beagles

Electrical impedance measurements were performed in splenectomized beagles according to the KUBICEK procedure using 4 dermal electrodes, which were placed in the midlines of the animals.

According to the pertinent literature, the comparability of absolute cardiac output values measured by bioimpedance method and thermodilution method was restricted.

Relative changes of cardiac output volumes measured by thermodilution and bioimpedance offered a better comparability. After infusions, thermodilution values differed significantly from cardiac output values measured by bioimpedance method.

In most cases, cardiac output measurements derived from the thermodilution method were higher than cardiac output values derived from bioimpedance method. Impedance curves showed a different shape in the ejection period between the first and the second heart sound.

Hence, transmediastinal impedance cardiography did not include impedance and volume changes of thoracic vessels depending on the "Windkesselfunktion" (air chamber function), blood viscosity, total peripheral resistance, etc. The method was proposed to measure volume changes of the heart in the ejection period.

Using the new developed procedure, cardiac output values derived from thermodilution compared favorably with cardiac output values derived from bioimpedance method.

Using the Kubicek method relative cardiac output changes were measured favorably.

Comparisons of single values, i.e. the initial value before the experiment, showed different results.

Using the new procedure, comparable results of single values could be achieved if compared with the thermodilution method.

The disclosure material of PCT application PCT/EP96/03918, filed Sep. 6, 1996, of which this application is a continuation and on which this application is based, is hereby incorporated into this application by reference.

We claim:

1. Procedure of determining cardiac output volume of a heart of a patient by sensing a varying systolic impedance of tissue of the heart, with at least one first measuring electrode (B) and at least a second measuring electrode (E-L), said procedure including the steps of: applying an electrical potential to the patient to thereby create a current flow through tissues of the heart; placing the first measuring electrode on the skin of the patient near the heart; inserting the second measuring electrode into a blood vessel at a position on an opposite side of the heart from the first measuring electrode so that a straight-line heart-traversing projection extending between the first and second measuring electrodes passes through the heart; sensing the varying systolic impedance of the heart with the first and second measuring electrodes.

2. Procedure according to claim 1, wherein is further included a depiction step for producing a picture of the second measuring electrode and the heart to properly position the second measuring electrode inside the blood vessel.

3. Procedure according to claim 1, wherein an electrocardiographic vector signal is produced and displayed to properly position the second measuring electrode in the blood vessel.

4. Procedure according to claim 1, wherein the first and second measuring electrodes are used for recording an electrocardiogram.

5. Procedure according to claim 4, wherein a plurality of second measuring electrodes are arranged on a catheter, with each second measuring electrode registering on an electrocardiogram, and wherein these electrocardiogram registrations are used to determine a specific second electrode whose straight-line projection with the first measuring electrode provides the best indication of heart impedance, and wherein the impedance variables determined by this specific second electrode are used for determining cardiac output volume.

6. Procedure according to claim 5, wherein several first measuring electrodes are placed on the skin, with each second measuring electrode having a straight-line heart traversing projection with one of the first measuring electrodes for sensing the varying systolic impedance of the heart along said straight-line heart traversing projection.

7. Procedure according to claim 1, wherein said electrical potential is applied to the patient by using first and second current driving electrodes and wherein said first current driving electrode is applied to the skin close to an apex of the heart.

8. Procedure according to claim 7, wherein said electrical potential is applied by arranging first and second current driving electrodes in such a manner that the straight-line projection between the first and second measuring electrodes conforms closely to a current path between the current driving electrodes.

9. Device for determining cardiac output volume of a heart of a patient by sensing a varying systolic impedance of tissue of the heart, wherein is included:

at least one first measuring electrode for being placed on the skin of the patient near his heart and a plurality of second measuring electrodes for being inserted into a body vessel of the patient at positions on an opposite side of the heart from the first measuring electrode so that straight-line heart-traversing projections extending between the first and second measuring electrodes pass through the heart;

a means for applying an electrical potential to the patient to thereby create a current flow through tissues of the heart;

electrocardiogram equipment; and cardiac output volume measuring equipment;

wherein said plurality of second measuring electrodes are arranged on a catheter, with each second measuring electrode being coupled to both the electrocardiogram equipment and the cardiac output volume measuring equipment, and wherein is further included a measuring means for evaluating electrocardiogram equipment registrations from the electrocardiogram equipment to determine a specific second electrode whose straight-line projection with the first measuring electrode provides the best indication of heart impedance and for then causing the cardiac output volume measuring equipment to use this specific second electrode to determine cardiac output volume.

10. Device according to claim 9, wherein the means for applying an electrical potential includes:

first and second current driving electrodes, with the first current driving electrode for being placed on the skin of the patient near his heart; and an alternating current generator coupled to the first and second current driving electrodes.

11. Device according to claim 9, wherein the catheter is a tube-like catheter in which said plurality of second measuring electrodes are axially spaced therealong on an outer cover thereof, said tube-like catheter defining an axial suction canal which is open to outside the catheter.

12. Device according to claim 11, wherein the tube-like catheter further includes an axial working canal for receiving an endoscope.

13. Device according to claim 11, wherein the plurality of second measuring catheters are approximately-equally spaced from one another along the tube-like catheter, and are electrically insulated from one another.

14. Device according to claim 9, wherein the means for applying an electrical potential includes first and second current driving electrodes and wherein the catheter is a tube-like catheter in which said second measuring electrodes and said second current driving electrode are axially arranged, the second measuring electrodes being arranged closer to a free end of the tube-like catheter than is the second current driving electrode.

15. Device according to claim 9, wherein said measuring electrodes are connected by a frequency switch so that a low-frequency part of a measured signal is fed to the electrocardiogram equipment and a high-frequency, impedance-alteration-representing part of the measuring signal is fed to the cardiac output volume measuring equipment.

* * * * *